United States Patent
Singh et al.

(10) Patent No.: US 9,186,449 B2
(45) Date of Patent: Nov. 17, 2015

(54) DIALYSIS MACHINE SUPPORT ASSEMBLIES AND RELATED SYSTEMS AND METHODS

(75) Inventors: Gurpreet Singh, Antioch, CA (US); Sean Farrell, Fresno, CA (US); Michael David Young, Antioch, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1051 days.

(21) Appl. No.: 13/286,586

(22) Filed: Nov. 1, 2011

(65) Prior Publication Data

US 2013/0106609 A1    May 2, 2013

(51) Int. Cl.
*A61M 1/00* (2006.01)
*A61M 1/28* (2006.01)

(52) U.S. Cl.
CPC ........... *A61M 1/28* (2013.01); *A61M 2205/121* (2013.01); *A61M 2205/128* (2013.01); *A61M 2209/084* (2013.01)

(58) Field of Classification Search
CPC ....... A61M 1/28; A61M 1/282; A61M 1/284; A47F 5/025; A47B 21/00; A47B 21/02; A47B 9/18; A47B 9/00; A47B 9/04; A47B 9/20; A47B 2009/185; A61G 7/00; A61G 7/002; A61G 7/012; A61G 13/02; A61G 13/06
USPC .......... 604/27–29; 108/20, 50.01, 50.02, 160, 108/106; 187/203–221; 248/637, 676, 679; 5/11, 600, 611
See application file for complete search history.

(56) References Cited

U.S. PATENT DOCUMENTS

| | | | |
|---|---|---|---|
| 3,927,955 A | 12/1975 | Spinosa et al. |
| 3,985,135 A | 10/1976 | Carpenter et al. |
| 4,026,669 A | 5/1977 | Leonard et al. |
| 4,303,376 A | 12/1981 | Siekmann |
| 4,370,983 A | 2/1983 | Lichtenstein |
| 4,382,753 A | 5/1983 | Archibald |
| 4,436,620 A | 3/1984 | Bellotti et al. |
| 4,453,932 A | 6/1984 | Pastrone |
| 4,479,762 A | 10/1984 | Bilstad et al. |
| 4,486,189 A | 12/1984 | Troutner et al. |
| 4,623,328 A | 11/1986 | Hartranft |
| 4,628,499 A | 12/1986 | Hammett |

(Continued)

FOREIGN PATENT DOCUMENTS

| | | |
|---|---|---|
| DE | 100 53 441 | 5/1916 |
| DE | 198 37 667 | 3/2000 |

(Continued)

OTHER PUBLICATIONS

Operator's Manual, Serena, Program Version 3.xx—English, 2002.

(Continued)

*Primary Examiner* — Edelmira Bosques
*Assistant Examiner* — Leah Swanson
(74) *Attorney, Agent, or Firm* — Fish & Richardson P.C.

(57) ABSTRACT

This application relates to a dialysis machine support assembly that includes a platform configured to support a dialysis machine and a drive assembly configured to move the platform vertically. A control unit can monitor input data from a sensor of the dialysis machine when the dialysis machine is supported by the platform and can operate the drive assembly to adjust a vertical position of the platform based on the input data.

23 Claims, 7 Drawing Sheets

(56) References Cited

U.S. PATENT DOCUMENTS

| | | | |
|---|---|---|---|
| 4,643,713 A | | 2/1987 | Viitala |
| 4,657,490 A | | 4/1987 | Abbott |
| 4,662,906 A | | 5/1987 | Matkovich et al. |
| 4,666,598 A | | 5/1987 | Heath et al. |
| 4,676,467 A | | 6/1987 | Palsulich |
| 4,710,166 A | | 12/1987 | Thompson et al. |
| 4,716,520 A | | 12/1987 | Locke et al. |
| 4,778,451 A | | 10/1988 | Kamen |
| 4,798,090 A | | 1/1989 | Heath et al. |
| 4,808,161 A | | 2/1989 | Kamen |
| 4,826,482 A | | 5/1989 | Kamen |
| 4,828,543 A | | 5/1989 | Weiss et al. |
| 4,840,542 A | | 6/1989 | Abbott |
| 4,872,635 A | * | 10/1989 | Knoblock et al. ......... 248/406.2 |
| 4,902,282 A | | 2/1990 | Bellotti et al. |
| 4,927,411 A | | 5/1990 | Pastrone et al. |
| 4,950,134 A | | 8/1990 | Bailey et al. |
| 4,976,162 A | | 12/1990 | Kamen |
| 4,997,464 A | | 3/1991 | Kopf |
| 5,002,471 A | | 3/1991 | Perlov |
| 5,036,886 A | | 8/1991 | Olsen et al. |
| 5,061,236 A | | 10/1991 | Sutherland et al. |
| 5,088,515 A | | 2/1992 | Kamen |
| 5,098,262 A | | 3/1992 | Wecker et al. |
| 5,100,380 A | | 3/1992 | Epstein et al. |
| 5,100,699 A | | 3/1992 | Roeser |
| 5,116,021 A | | 5/1992 | Faust et al. |
| 5,116,316 A | | 5/1992 | Sertic et al. |
| 5,146,713 A | | 9/1992 | Grafius |
| 5,151,019 A | | 9/1992 | Danby et al. |
| 5,167,837 A | | 12/1992 | Snodgrass et al. |
| 5,171,029 A | | 12/1992 | Maxwell et al. |
| 5,178,182 A | | 1/1993 | Kamen |
| 5,187,990 A | | 2/1993 | Magnussen et al. |
| 5,193,990 A | | 3/1993 | Kamen et al. |
| 5,211,201 A | | 5/1993 | Kamen et al. |
| 5,241,985 A | | 9/1993 | Faust et al. |
| 5,247,434 A | | 9/1993 | Peterson et al. |
| 5,250,027 A | | 10/1993 | Lewis et al. |
| 5,252,044 A | | 10/1993 | Raines et al. |
| 5,259,326 A | * | 11/1993 | Borgman et al. ............. 108/147 |
| 5,279,556 A | | 1/1994 | Goi et al. |
| 5,302,093 A | | 4/1994 | Owens et al. |
| 5,311,908 A | | 5/1994 | Barone et al. |
| 5,315,632 A | | 5/1994 | Flynn et al. |
| 5,324,422 A | | 6/1994 | Colleran et al. |
| 5,330,425 A | | 7/1994 | Utterberg |
| 5,350,357 A | | 9/1994 | Kamen et al. |
| D351,470 S | | 10/1994 | Scherer et al. |
| 5,353,837 A | | 10/1994 | Faust |
| 5,395,351 A | | 3/1995 | Munsch |
| 5,421,208 A | | 6/1995 | Packard et al. |
| 5,421,823 A | | 6/1995 | Kamen et al. |
| 5,427,509 A | | 6/1995 | Chapman et al. |
| 5,431,626 A | | 7/1995 | Bryant et al. |
| 5,431,627 A | | 7/1995 | Pastrone et al. |
| 5,431,634 A | | 7/1995 | Brown |
| 5,438,510 A | | 8/1995 | Bryant et al. |
| 5,441,636 A | | 8/1995 | Chevallet et al. |
| 5,445,506 A | | 8/1995 | Afflerbaugh et al. |
| 5,447,286 A | | 9/1995 | Kamen et al. |
| 5,450,743 A | | 9/1995 | Buote |
| 5,461,974 A | * | 10/1995 | Reneau ........................ 108/147 |
| 5,462,416 A | | 10/1995 | Dennehey et al. |
| 5,462,417 A | | 10/1995 | Chapman |
| 5,474,683 A | | 12/1995 | Bryant et al. |
| 5,478,211 A | | 12/1995 | Dominiak et al. |
| 5,480,294 A | | 1/1996 | Di Perna et al. |
| 5,482,438 A | | 1/1996 | Anderson et al. |
| 5,482,440 A | | 1/1996 | Dennehey et al. |
| 5,482,446 A | | 1/1996 | Williamson et al. |
| 5,484,239 A | | 1/1996 | Chapman et al. |
| 5,486,286 A | | 1/1996 | Peterson et al. |
| 5,514,069 A | | 5/1996 | Brown et al. |
| 5,514,102 A | | 5/1996 | Winterer et al. |
| 5,526,756 A | * | 6/1996 | Watson ........................ 108/147 |
| 5,538,405 A | | 7/1996 | Patno et al. |
| 5,547,453 A | | 8/1996 | Di Perna |
| 5,551,850 A | | 9/1996 | Williamson et al. |
| 5,551,941 A | | 9/1996 | Howell |
| 5,551,942 A | | 9/1996 | Brown et al. |
| 5,554,013 A | | 9/1996 | Owens et al. |
| 5,570,716 A | | 11/1996 | Kamen et al. |
| 5,578,070 A | | 11/1996 | Utterberg |
| 5,609,572 A | | 3/1997 | Lang |
| 5,614,677 A | | 3/1997 | Wamsiedler et al. |
| 5,628,908 A | | 5/1997 | Kamen et al. |
| 5,630,710 A | | 5/1997 | Tune et al. |
| 5,634,896 A | | 6/1997 | Bryant et al. |
| 5,640,995 A | | 6/1997 | Packard et al. |
| 5,641,405 A | | 6/1997 | Keshaviah et al. |
| 5,641,892 A | | 6/1997 | Larkins et al. |
| 5,643,205 A | | 7/1997 | Utterberg |
| 5,658,133 A | | 8/1997 | Anderson et al. |
| 5,690,602 A | | 11/1997 | Brown et al. |
| D390,654 S | | 2/1998 | Alsberg et al. |
| 5,713,865 A | | 2/1998 | Manning et al. |
| 5,713,888 A | | 2/1998 | Neuenfeldt et al. |
| 5,741,125 A | | 4/1998 | Neftel et al. |
| 5,746,708 A | | 5/1998 | Giesler et al. |
| 5,755,683 A | | 5/1998 | Houle et al. |
| 5,764,034 A | | 6/1998 | Bowman et al. |
| 5,771,914 A | | 6/1998 | Ling et al. |
| 5,772,635 A | | 6/1998 | Dastur et al. |
| 5,772,637 A | | 6/1998 | Heinzmann et al. |
| 5,782,805 A | | 7/1998 | Meinzer et al. |
| 5,799,207 A | | 8/1998 | Wang et al. |
| 5,816,779 A | | 10/1998 | Lawless et al. |
| 5,906,598 A | | 5/1999 | Giesler et al. |
| 5,935,099 A | | 8/1999 | Peterson et al. |
| 5,938,634 A | | 8/1999 | Packard |
| 5,989,423 A | | 11/1999 | Kamen |
| 5,993,174 A | | 11/1999 | Konishi |
| 5,996,634 A | | 12/1999 | Dennehey et al. |
| 6,013,057 A | | 1/2000 | Danby et al. |
| 6,036,668 A | | 3/2000 | Mathis |
| 6,036,680 A | | 3/2000 | Horne et al. |
| 6,041,801 A | | 3/2000 | Gray et al. |
| 6,065,941 A | | 5/2000 | Gray et al. |
| 6,068,612 A | | 5/2000 | Bowman et al. |
| 6,074,359 A | | 6/2000 | Keshaviah et al. |
| 6,099,492 A | | 8/2000 | Le Boeuf |
| 6,118,207 A | | 9/2000 | Ormerod et al. |
| 6,129,517 A | | 10/2000 | Danby et al. |
| 6,136,565 A | | 10/2000 | Best et al. |
| 6,154,605 A | | 11/2000 | Aonuma |
| 6,164,621 A | | 12/2000 | Bouchard et al. |
| 6,165,154 A | | 12/2000 | Gray et al. |
| 6,179,801 B1 | | 1/2001 | Holmes et al. |
| 6,184,356 B1 | | 2/2001 | Anderson et al. |
| 6,196,987 B1 | | 3/2001 | Holmes et al. |
| 6,200,287 B1 | | 3/2001 | Keller et al. |
| 6,208,107 B1 | | 3/2001 | Maske et al. |
| 6,220,295 B1 | | 4/2001 | Bouchard et al. |
| 6,223,130 B1 | | 4/2001 | Gray et al. |
| 6,227,807 B1 | | 5/2001 | Chase |
| 6,228,047 B1 | | 5/2001 | Dadson |
| 6,231,537 B1 | | 5/2001 | Holmes et al. |
| 6,234,989 B1 | | 5/2001 | Brierton et al. |
| 6,250,502 B1 | | 6/2001 | Cote et al. |
| 6,261,065 B1 | | 7/2001 | Nayak et al. |
| 6,267,242 B1 | | 7/2001 | Nagata et al. |
| 6,270,673 B1 | | 8/2001 | Belt et al. |
| 6,280,406 B1 | | 8/2001 | Dolecek et al. |
| 6,281,145 B1 | | 8/2001 | Deguchi et al. |
| 6,284,142 B1 | | 9/2001 | Muller |
| 6,285,155 B1 | | 9/2001 | Maske et al. |
| 6,294,094 B1 | | 9/2001 | Muller et al. |
| 6,296,450 B1 | | 10/2001 | Westberg et al. |
| 6,297,322 B1 | | 10/2001 | Ding et al. |
| 6,315,707 B1 | | 11/2001 | Smith et al. |
| 6,316,864 B1 | | 11/2001 | Ormerod |
| 6,322,488 B1 | | 11/2001 | Westberg et al. |
| 6,325,775 B1 | | 12/2001 | Thom et al. |

(56) References Cited

U.S. PATENT DOCUMENTS

| | | |
|---|---|---|
| 6,337,049 B1 | 1/2002 | Tamari |
| RE37,553 E | 2/2002 | Ciavarini et al. |
| 6,343,614 B1 | 2/2002 | Gray et al. |
| 6,348,156 B1 | 2/2002 | Vishnoi et al. |
| 6,361,518 B1 | 3/2002 | Brierton et al. |
| 6,364,857 B1 | 4/2002 | Gray et al. |
| 6,382,923 B1 | 5/2002 | Gray |
| 6,383,158 B1 | 5/2002 | Utterberg |
| 6,406,276 B1 | 6/2002 | Normand et al. |
| 6,409,696 B1 | 6/2002 | Toavs et al. |
| 6,416,293 B1 | 7/2002 | Bouchard et al. |
| 6,419,822 B2 | 7/2002 | Muller et al. |
| 6,455,676 B1 | 9/2002 | Weickert et al. |
| 6,471,855 B1 | 10/2002 | Odak et al. |
| 6,481,980 B1 | 11/2002 | Vandlik et al. |
| 6,489,896 B1 | 12/2002 | Platt et al. |
| 6,491,656 B1 | 12/2002 | Morris |
| 6,497,674 B1 | 12/2002 | Steele et al. |
| 6,497,676 B1 | 12/2002 | Childers et al. |
| 6,503,062 B1 | 1/2003 | Gray et al. |
| 6,514,225 B1 | 2/2003 | Utterberg et al. |
| 6,519,569 B1 | 2/2003 | White et al. |
| 6,520,747 B2 | 2/2003 | Gray et al. |
| 6,524,231 B1 | 2/2003 | Westberg et al. |
| 6,537,445 B2 | 3/2003 | Muller |
| 6,542,761 B1 | 4/2003 | Jahn et al. |
| 6,558,343 B1 | 5/2003 | Neftel |
| 6,572,604 B1 | 6/2003 | Platt et al. |
| 6,592,542 B2 | 7/2003 | Childers et al. |
| 6,595,948 B2 | 7/2003 | Suzuki et al. |
| 6,603,229 B1 | 8/2003 | Toye, IV |
| 6,604,908 B1 | 8/2003 | Bryant et al. |
| 6,645,166 B2 | 11/2003 | Scheunert et al. |
| 6,645,177 B1 | 11/2003 | Shearrn |
| 6,648,861 B2 | 11/2003 | Platt et al. |
| 6,663,359 B2 | 12/2003 | Gray |
| 6,670,323 B1 | 12/2003 | Looker et al. |
| 6,695,803 B1 | 2/2004 | Robinson et al. |
| 6,709,417 B1 | 3/2004 | Houle et al. |
| 6,716,004 B2 | 4/2004 | Vandlik et al. |
| 6,723,062 B1 | 4/2004 | Westberg et al. |
| 6,725,726 B1 | 4/2004 | Adolfs et al. |
| 6,726,656 B2 | 4/2004 | Kamen et al. |
| 6,730,055 B2 | 5/2004 | Bainbridge et al. |
| 6,743,201 B1 | 6/2004 | Donig et al. |
| 6,746,514 B2 | 6/2004 | Bedingfield et al. |
| 6,749,403 B2 | 6/2004 | Bryant et al. |
| 6,752,172 B2 | 6/2004 | Lauer |
| 6,755,801 B2 | 6/2004 | Utterberg et al. |
| 6,758,975 B2 | 7/2004 | Peabody et al. |
| 6,759,007 B1 | 7/2004 | Westberg et al. |
| 6,764,460 B2 | 7/2004 | Dolecek et al. |
| 6,764,761 B2 | 7/2004 | Eu et al. |
| 6,768,425 B2 | 7/2004 | Flaherty et al. |
| 6,774,517 B2 | 8/2004 | Kowalski et al. |
| 6,790,195 B2 | 9/2004 | Steele et al. |
| 6,790,198 B1 | 9/2004 | White et al. |
| 6,800,054 B2 | 10/2004 | Westberg et al. |
| 6,808,369 B2 | 10/2004 | Gray et al. |
| 6,814,547 B2 | 11/2004 | Childers et al. |
| 6,821,432 B2 | 11/2004 | Metzner |
| 6,828,125 B1 | 12/2004 | Hoffman et al. |
| 6,846,161 B2 | 1/2005 | Kline et al. |
| 6,852,090 B2 | 2/2005 | Burbank et al. |
| 6,869,538 B2 | 3/2005 | Yu et al. |
| 6,905,479 B1 | 6/2005 | Bouchard et al. |
| 6,929,751 B2 | 8/2005 | Bowman, Jr. et al. |
| 6,939,111 B2 | 9/2005 | Huitt et al. |
| 6,949,079 B1 | 9/2005 | Westberg et al. |
| 6,953,323 B2 | 10/2005 | Childers et al. |
| 6,969,373 B2 | 11/2005 | Schwartz et al. |
| 6,984,218 B2 | 1/2006 | Nayak et al. |
| 7,021,148 B2 | 4/2006 | Kuhn et al. |
| 7,033,539 B2 | 4/2006 | Krensky et al. |
| 7,041,076 B1 | 5/2006 | Westberg et al. |
| 7,044,432 B2 | 5/2006 | Beden et al. |
| 7,049,406 B2 | 5/2006 | Weickert et al. |
| 7,083,719 B2 | 8/2006 | Bowman, Jr. et al. |
| 7,087,036 B2 | 8/2006 | Busby et al. |
| 7,107,837 B2 | 9/2006 | Lauman et al. |
| 7,115,107 B2 | 10/2006 | Delnevo et al. |
| 7,115,228 B2 | 10/2006 | Lundtveit et al. |
| 7,147,613 B2 | 12/2006 | Burbank et al. |
| 7,153,286 B2 | 12/2006 | Busby et al. |
| 7,160,087 B2 | 1/2007 | Fathallah et al. |
| 7,166,231 B2 | 1/2007 | Westberg et al. |
| 7,175,606 B2 | 2/2007 | Bowman, Jr. et al. |
| 7,195,607 B2 | 3/2007 | Westberg et al. |
| 7,211,560 B2 | 5/2007 | Looker et al. |
| 7,232,435 B2 | 6/2007 | Hildebrand et al. |
| 7,236,936 B2 | 6/2007 | White et al. |
| 7,238,164 B2 | 7/2007 | Childers et al. |
| 7,255,680 B1 | 8/2007 | Gharib |
| 7,258,534 B2 | 8/2007 | Fathallah et al. |
| 7,267,661 B2 | 9/2007 | Susi |
| 7,338,472 B2 | 3/2008 | Shearn |
| 7,345,025 B2 | 3/2008 | Symonds et al. |
| 7,347,836 B2 | 3/2008 | Peterson et al. |
| 7,390,311 B2 | 6/2008 | Hildebrand et al. |
| 7,398,183 B2 | 7/2008 | Holland et al. |
| 7,399,637 B2 | 7/2008 | Wright et al. |
| 7,404,809 B2 | 7/2008 | Susi |
| 7,410,475 B2 | 8/2008 | Krensky et al. |
| 7,422,905 B2 | 9/2008 | Clague et al. |
| 7,454,314 B2 | 11/2008 | Holland et al. |
| 7,490,021 B2 | 2/2009 | Holland et al. |
| 7,500,962 B2 | 3/2009 | Childers et al. |
| 7,517,387 B2 | 4/2009 | Chevallet et al. |
| 7,553,295 B2 | 6/2009 | Susi |
| 7,556,616 B2 | 7/2009 | Fathallah et al. |
| 7,575,564 B2 | 8/2009 | Childers |
| 7,618,948 B2 | 11/2009 | Kaemmerer |
| 7,645,258 B2 | 1/2010 | White et al. |
| 7,648,627 B2 | 1/2010 | Beden et al. |
| 7,654,976 B2 | 2/2010 | Peterson et al. |
| 7,662,286 B2 | 2/2010 | Childers et al. |
| 7,699,966 B2 | 4/2010 | Qin et al. |
| 7,789,849 B2 | 9/2010 | Busby et al. |
| 7,815,595 B2 | 10/2010 | Busby et al. |
| 2001/0034502 A1 | 10/2001 | Moberg |
| 2001/0037763 A1 | 11/2001 | Deguchi et al. |
| 2002/0045851 A1 | 4/2002 | Suzuki et al. |
| 2002/0062105 A1 | 5/2002 | Tanner et al. |
| 2002/0062109 A1 | 5/2002 | Lauer |
| 2002/0072718 A1 | 6/2002 | Brugger et al. |
| 2002/0107474 A1 | 8/2002 | Noack |
| 2002/0147423 A1 | 10/2002 | Burbank et al. |
| 2003/0018395 A1 | 1/2003 | Crnkovich et al. |
| 2003/0028144 A1 | 2/2003 | Duchon et al. |
| 2003/0029451 A1 | 2/2003 | Blair et al. |
| 2003/0042181 A1 | 3/2003 | Metzner |
| 2003/0100882 A1 | 5/2003 | Beden et al. |
| 2003/0136189 A1 | 7/2003 | Lauman et al. |
| 2003/0200812 A1 | 10/2003 | Kuhn et al. |
| 2003/0204162 A1 | 10/2003 | Childers et al. |
| 2003/0217957 A1 | 11/2003 | Bowman et al. |
| 2003/0217961 A1 | 11/2003 | Hopping |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0220608 A1 | 11/2003 | Huitt et al. |
| 2003/0220609 A1* | 11/2003 | Childers et al. .................. 604/29 |
| 2003/0220627 A1 | 11/2003 | Distler et al. |
| 2004/0010223 A1 | 1/2004 | Busby et al. |
| 2004/0019313 A1 | 1/2004 | Childers et al. |
| 2004/0019320 A1 | 1/2004 | Childers et al. |
| 2004/0031756 A1 | 2/2004 | Suzuki et al. |
| 2004/0064080 A1 | 4/2004 | Cruz et al. |
| 2004/0067161 A1 | 4/2004 | Axelsson |
| 2004/0082903 A1 | 4/2004 | Micheli |
| 2004/0084647 A1 | 5/2004 | Beden et al. |
| 2004/0135078 A1 | 7/2004 | Mandro et al. |

(56) References Cited

U.S. PATENT DOCUMENTS

| | | |
|---|---|---|
| 2004/0156745 A1 | 8/2004 | Vandlik et al. |
| 2004/0195190 A1 | 10/2004 | Min et al. |
| 2004/0238416 A1 | 12/2004 | Burbank et al. |
| 2005/0054968 A1 | 3/2005 | Giannella |
| 2005/0165354 A1 | 7/2005 | Schwartz et al. |
| 2005/0209563 A1 | 9/2005 | Hopping et al. |
| 2005/0230292 A1 | 10/2005 | Beden et al. |
| 2006/0079826 A1 | 4/2006 | Beden et al. |
| 2006/0195064 A1 | 8/2006 | Plahey et al. |
| 2007/0112297 A1 | 5/2007 | Plahey et al. |
| 2007/0149913 A1 | 6/2007 | Busby et al. |
| 2007/0193940 A1 | 8/2007 | Duchamp et al. |
| 2007/0213651 A1 | 9/2007 | Busby et al. |
| 2007/0213653 A1 | 9/2007 | Childers et al. |
| 2007/0213654 A1 | 9/2007 | Lundtveit et al. |
| 2007/0269340 A1 | 11/2007 | Dannenmaier et al. |
| 2008/0033346 A1 | 2/2008 | Childers et al. |
| 2008/0077068 A1 | 3/2008 | Orr |
| 2008/0208103 A1 | 8/2008 | Demers et al. |
| 2009/0004033 A1 | 1/2009 | Demers et al. |
| 2009/0300845 A1 * | 12/2009 | Paz et al. ................. 5/610 |
| 2010/0120006 A1 * | 5/2010 | Bell et al. ................. 434/267 |
| 2011/0040242 A1 | 2/2011 | Fallon et al. |
| 2011/0185722 A1 | 8/2011 | Sebesta et al. |

FOREIGN PATENT DOCUMENTS

| | | |
|---|---|---|
| DE | 100 42 324 | 2/2002 |
| DE | 100 46 651 | 4/2002 |
| DE | 101 57 924 | 5/2002 |
| DE | 101 43 137 | 4/2003 |
| EP | 0728509 | 8/1996 |
| EP | 0856321 | 8/1998 |
| EP | 0 947 814 B2 | 10/1999 |
| EP | 0 956 876 A1 | 11/1999 |
| EP | 1529545 | 5/2005 |
| JP | 04-191755 | 7/1992 |
| JP | 06-002650 | 1/1994 |
| JP | 06-154314 | 6/1994 |
| JP | 11-347115 | 12/1999 |
| JP | 2000-070358 | 3/2000 |
| WO | WO 84/02473 | 7/1984 |
| WO | WO 86/01115 | 2/1986 |
| WO | WO 97/16214 | 5/1997 |
| WO | WO 97/37703 | 10/1997 |
| WO | WO 98/22165 | 5/1998 |
| WO | WO 00/23140 | 4/2000 |
| WO | WO 00/33898 | 6/2000 |
| WO | WO 01/17605 | 3/2001 |
| WO | WO 02/25225 | 3/2002 |
| WO | WO2011091975 A1 | 8/2011 |

OTHER PUBLICATIONS

Acumen, "Acute Dialysis Machine Brief Operating Instructions," Software Version 1.0, pp. 1-146, Oct. 5, 1996.

Gambro®, Prisma® HF 1000, "For Increased Filtration Capacity", © Aug. 2001, Gambro Renal Products, Inc., Lakewood, CO, 2 pp.

Gambro®, "DEHP-Free Cartridge Blood Sets," © Nov. 2004, Gambro, Inc., Lakewood, CO, 4 pp.

Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.

Gambro®, "Prismaflex™ Anticipating Critical Care needs and taking our innovative resonse to new heights," © 2004, Gambro Inc., Lakewood, CO, 8 pp.

Glenn Avolio, "Principles of Rotary Optical Encoders," Sensors Journal of Machine Perception, vol. 10,1 No. 4, pp. 10-18, 1993.

Liberty Cycler User's Guide©, 2008, pp. 1-174.

Manns, Markus et al, "The acu-men: A new device for continuous renal replacement therapy in acute renal failure," Kidney International, vol. 54, pp. 268-274, 1998.

Newton IQ Cycler Operator Manual, Part No. 470203 Rev. F, 2000-2006.

Operator's Instructions, Fresenius 90/2 Peritoneal Therapy Cycler, Part No. 470016 Rev. B, 1991.

Operator's Manual, Serena, Program Version 3.xx—English.

Sleep Safe Operating Instructions, Software Version 0.9, Part No. 677 805 1, Fresenius Medical Care, Aug. 2000.

Sleep Safe Technical Manual, Part No. 677 807 1, Aug. 2000.

* cited by examiner

DIALYSIS MACHINE SUPPORT ASSEMBLIES AND RELATED SYSTEMS AND METHODS

TECHNICAL FIELD

This invention relates to dialysis machine support assemblies and related systems and methods.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semipermeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal of waste products, including solutes like urea and creatinine, from the blood, and regulate the levels of other substances, such as sodium and water, in the blood.

Many PD cyclers are designed to automatically infuse, dwell, and drain dialysate to and from the patient's peritoneal cavity. The treatment typically lasts for several hours, often beginning with an initial drain procedure to empty the peritoneal cavity of used or spent dialysate. The sequence then proceeds through the succession of fill, dwell, and drain phases that follow one after the other. Each phase is called a cycle.

SUMMARY

In one aspect of the invention, a dialysis machine support assembly includes a platform configured to support a dialysis machine, and a drive assembly configured to move the platform vertically.

Implementations can include one or more of the following features.

In some implementations, the drive assembly is configured to be controlled by the dialysis machine.

In some implementations, the drive assembly can move the platform along a vertical distance that is 24-48 inches.

In some implementations, the dialysis machine support assembly includes a control unit that is electrically connected to the drive assembly and is configured to operate the drive assembly to move and position the platform vertically.

In some implementations, the dialysis machine support assembly includes a device configured to prevent the platform from rotating about the drive assembly when the platform moves vertically.

In some implementations, the drive assembly includes a leadscrew fixed to a base, a leadscrew nut that is rotatably coupled to the platform and configured to engage the leadscrew, and a motor that is mechanically connected to the leadscrew nut and configured to rotate the leadscrew nut.

In some implementations, the motor is an electric motor configured to be electrically connected to the dialysis machine or to an external control unit.

In some implementations, the leadscrew has a recess formed longitudinally along the leadscrew, and the platform has a tab that is sized to fit within the recess and travel along the recess when the platform moves vertically.

In some implementations, the dialysis machine support assembly includes multiple legs and a stationary platform disposed on top of the multiple legs.

In some implementations, the dialysis machine support assembly includes a base from which the multiple legs extend upwardly.

In some implementations, the dialysis machine support assembly includes multiple wheels secured to the bottom of the base to support the dialysis machine support assembly.

In another aspect of the invention, a dialysis system includes a dialysis machine; and a dialysis machine support assembly that includes a platform configured to support the dialysis machine, and a drive assembly configured to move the platform vertically, where the dialysis machine is disposed on the platform.

Implementations can include one or more of the following features.

In some implementations, the dialysis machine is electrically connected to the drive assembly and configured to operate the drive assembly to move and position the platform vertically.

In some implementations, the dialysis machine includes pressure sensors to measure pressure in a fluid path between fluid pump chambers of the dialysis machine and a patient.

In some implementations, the dialysis machine is a peritoneal dialysis cycler.

In another aspect of the invention, a dialysis machine support assembly includes a base, multiple wheels disposed along a bottom surface of the base, a drive assembly extending upward from the base that is configured to be electrically connected to a dialysis machine, a vertically moveable platform secured to a moving portion of the drive assembly, the vertically moveable platform being configured to support the dialysis machine, and the position of the vertically moveable platform being controlled by the drive assembly, multiple legs extending upward from the base, a stationary platform disposed on top of the multiple legs, the stationary platform defining a recess that is sized to receive the vertically moveable platform, and multiple hooks extending from the sides of the stationary platform, the hooks being configured to support dialysate bags fluidly connected to the dialysis machine during a dialysis treatment, where the drive assembly is configured to move the vertically moveable platform above and below a height at which a patient is positioned during a dialysis treatment.

In a further aspect of the invention, a method includes monitoring pressure in a fluid path between a dialysis fluid pump chamber and a patient, and adjusting a vertical position of a dialysis machine when monitored pressure exceeds a maximum pressure or falls below a minimum pressure.

Implementations can include one or more of the following features.

In some implementations, the method further includes adjusting a rate at which fluid is pump to or from a patient along the fluid path.

In some implementations, adjusting a vertical position when monitored pressure exceeds a maximum pressure includes moving the dialysis machine upward vertically while fluid is being provided to a patient.

In some implementations, the maximum pressure is 150-200 mbar.

In some implementations, the method further includes reducing a rate at which fluid is pumped to the patient.

In some implementations, adjusting a vertical position when monitored pressure falls below a minimum pressure includes moving the dialysis machine downward vertically while fluid is being removed from a patient.

In some implementations, the minimum pressure is (−150)-(−200) mbar.

In some implementations, the method further includes reducing a rate at which fluid is pumped from the patient.

Implementations can include one or more of the following advantages.

Systems and methods described herein can be used to optimize filling and draining cycles of dialysis treatments by raising and/or lowering a dialysis cycler relative to a patient in order to maximize flow rates of dialysis solution.

Additionally, methods described herein can be used to avoid signaling alarms and/or disturbing a patient during dialysis treatments by automatically responding to elevated, potentially dangerous levels of fluid resistance measured within a patient line during filling and draining cycles of dialysis treatments by raising and/or lowering a dialysis cycler relative to a patient.

DETAILED DESCRIPTION

This disclosure relates generally to dialysis machine support assemblies and related systems and methods. In some cases, a dialysis machine support assembly (e.g., a cart) includes a vertically movable platform configured to support a dialysis machine (e.g., a PD cycler). During dialysis treatments, the dialysis machine can be seated on the platform that moves vertically relative to a patient. The height of the platform and the dialysis machine can be controlled based on the pressure or resistance measured within a fluid line or compartment located along a fluid flow path between the dialysis machine and the patient. For example, the height of the platform and the dialysis machine can be controlled in a manner to maintain a desired flow rate of fluid passing from the dialysis machine to the patient or vice versa. The dialysis machine support assembly can be used to safely and effectively accommodate for spikes in fluid resistance pressure within lines connected to the patient, which could otherwise cause an alarm that would disturb the patient and require attention. The systems and methods described herein of using the cart during dialysis treatments to raise and lower the dialysis machine can be used to optimize the flow of fluid to and/or from the patient.

Figure 1:
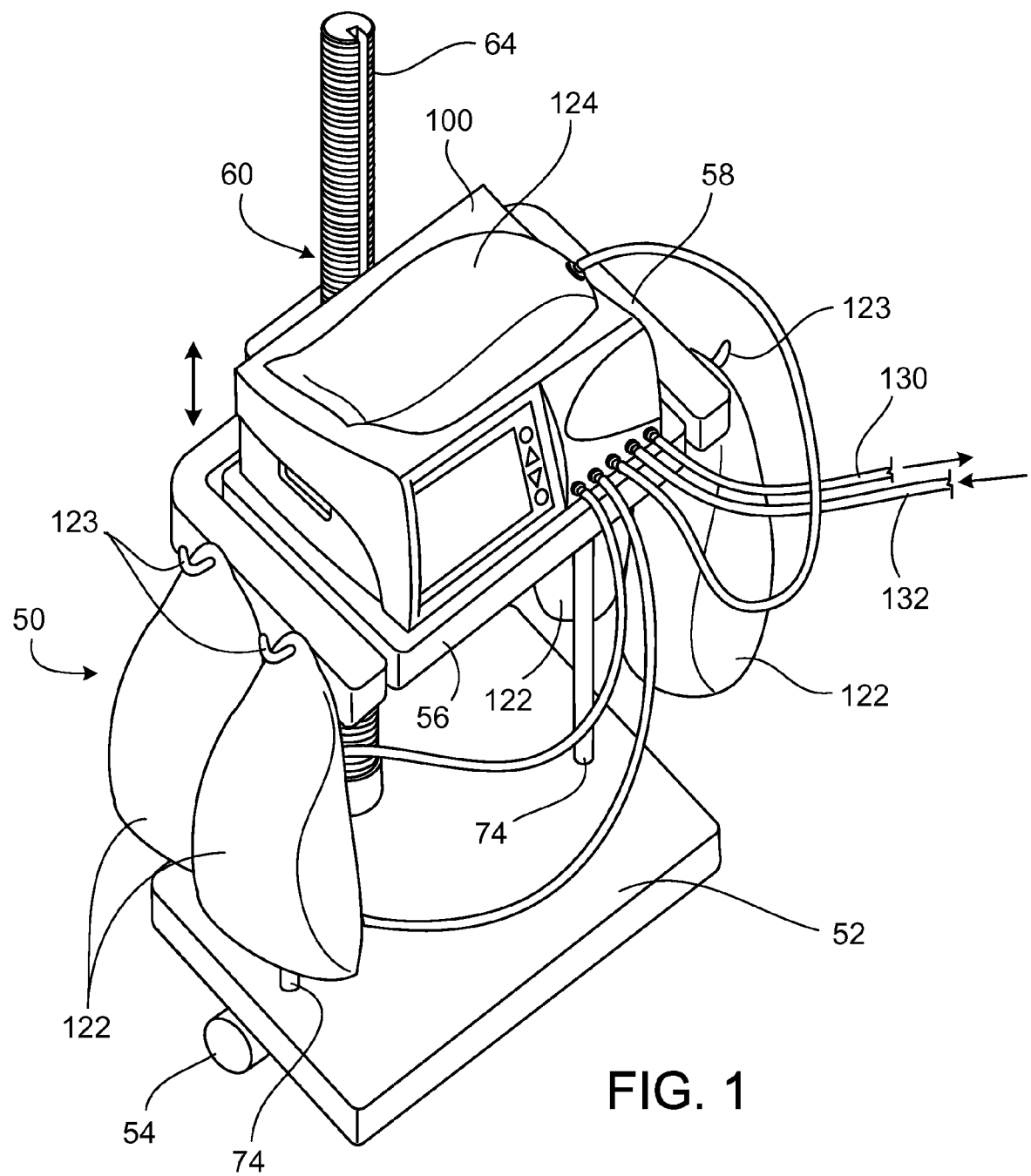
FIG. 1 is a perspective view of a peritoneal dialysis (PD) cycler on a cart that has a vertically moveable platform.

FIG. 1 shows a PD cycler 100 seated on a cart 50. As discussed herein, the PD cycler 100 is used to deliver PD solution (e.g., dialysate) to and drain fluid from a patient during PD treatments.

Cart

Figure 2:
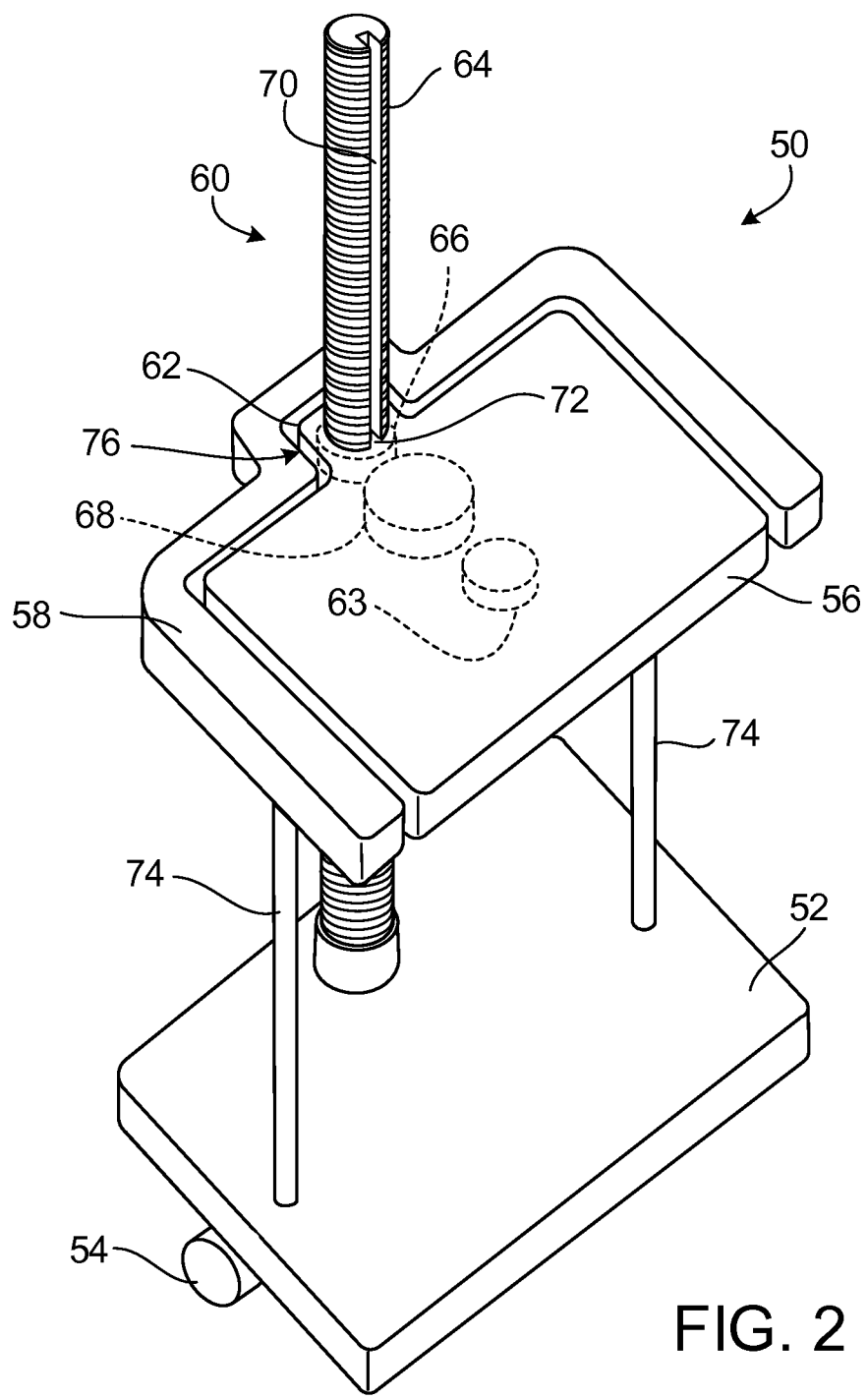
FIG. 2 is a perspective view of the cart of FIG. 1.

As shown in FIG. 2, the cart 50 includes a base 52, multiple (e.g., three) wheels 54, a vertically moveable platform 56, a table platform 58, and a drive assembly 60 to move the vertically moveable platform 56 upward and downward.

The base 52 is a substantially flat, planar member that is mounted on top of the wheels 54 and provides a mounting location for the other components of the cart 50, including the table platform 58 and the drive assembly 60. The base 52 is typically about 8 inches to about 24 inches (e.g., about 8 inches to 11 inches) wide by 6 inches to about 20 inches (e.g., 7 inches to 10 inches) deep and can be formed (e.g., molded, machined, and/or cast) of any of various suitable materials (e.g., plastics, metals, and/or composites). The base 52 is designed to sufficiently support the other components of the cart 50. For example, the base can be made to support typically about 25 lbs to about 100 lbs.

The wheels 54 are fastened to the bottom of the base 52 so that the cart 50 can be moved smoothly along typical floor surfaces. The wheels 54 are typically casters (e.g., rigid or swivel casters) that can be made of any of various suitable materials (e.g., plastics, metals, and/or composites).

The vertically moveable platform 56 is a substantially flat planar member, similar to the base 52, that provides a seating location for the PD cycler 100. The vertically moveable platform 56 is typically about 8 inches to about 24 inches (e.g., about 8 inches to 11 inches) wide by 6 inches to about 20 inches (e.g., 7 inches to 10 inches) deep and can be formed (e.g., molded, machined, and/or cast) of any of various suitable materials (e.g., plastics, metals, and/or composites). The vertically moveable platform 56 is designed to sufficiently support the weight of the PD cycler 100 while stationary, as well as when articulating up and down. For example, the vertically moveable platform can be made to support typically about 35 lbs to about 60 lbs. During PD treatments, the vertically moveable platform 56 moves up and down via the drive assembly 60, as discussed below. The vertically moveable platform 56 also includes an extension 62 that contains certain components of the drive assembly 60, as discussed below.

The drive assembly 60 is used to move the vertically moveable platform 56 and the PD cycler 100 seated on the vertically moveable platform 56 up and down in a controlled and monitored manner during PD treatments. The drive assembly 60 is configured to move the vertically moveable platform 56 over a height range that is typically greater than 24 inches (e.g., about 24 inches to about 48 inches). The drive assembly 60 includes a leadscrew 64 and a leadscrew nut 66 that is rotated and controlled by a motor 68 during articulation. The leadscrew 64 is mounted to the base 52 in a fixed position and extends upward from the base 52. The motor 68 and leadscrew nut 66 are contained in the vertically moveable platform 56. As shown, the leadscrew nut 66 is positioned in the extension 62 of the vertically moveable platform 56 so that it can engage the leadscrew 64. The leadscrew nut 66 is coupled to the extension 62 such that the leadscrew nut 66 is able to rotate about its central axis with respect to the vertically moveable platform 56 and the extension 62 (e.g., via bearings that connect the leadscrew nut 66 to vertically moveable platform 56), but it is constrained from moving in a vertical direction with respect to the vertically moveable platform 56 and the extension 62. Therefore, as the electric motor 68 rotates the leadscrew nut 66, the leadscrew nut 66 rotates about the stationary leadscrew 64 and therefore travels upward or downward along threads of the leadscrew 64 depending on the direction of rotation of the leadscrew nut 66.

The drive assembly 60 includes an alignment mechanism that prevents the vertically moveable platform 56 from rotating around the leadscrew 64 as the leadscrew nut 66 rotates. Although the leadscrew nut 66 is typically able to rotate freely within the extension 62 of the vertically moveable platform 56, frictional and/or inertial forces caused by the rotating leadscrew nut 66 could potentially cause the vertically moveable platform 56 to also rotate about the leadscrew 64. To prevent rotation of the vertically moveable platform 56, the leadscrew 64 includes a recessed channel 70 within the leadscrew threads that extends uniformly along the longitudinal direction of the leadscrew 64. To engage the recessed channel 70, the vertically moveable platform 56 includes a tab feature 72 that is sized to fit within the recessed channel 70. As the leadscrew nut 66 rotates around the stationary leadscrew 64 and articulates upward or downward, the tab 72 moves vertically within the recessed channel 70 and prevents the vertically moveable platform 56 from rotating. In some examples, the tab 72 includes linear bushings or bearings to provide smooth translation along the recess 70.

The motor 68 is an electric motor (e.g., an electric stepper motor, other types of DC motors, or an AC motor) that is mechanically connected to the leadscrew nut 66 using gears to provide rotation to the leadscrew nut 66. The motor 68 includes electrical connections (e.g., wiring and/or a wire harness) to electrically connect the motor 68 to the PD cycler 100 to be used with the cart so that the PD cycler 100 can control the motion as well as monitor the position of the vertically moveable platform 56. During use, the PD cycler 100 can monitor the position of the vertically moveable platform 56 by monitoring the rotation of the motor 68. By knowing an initial position (e.g., a home position) of the vertically moveable platform 56, the PD cycler 100 can count the number of stepper motor rotations or steps in order to calculate the upward or downward travel and therefore the position of the vertically moveable platform 56. By monitoring the number of motor steps, the distance of upward or downward travel of the vertically moveable platform 56 can be determined using the pitch of the leadscrew threads. To calibrate the cart 50 and the PD cycler 100, the initial position (e.g., the height during assembly or installation) of the vertically moveable platform 56 and the distance that the vertically moveable platform 56 travels during each motor step can be coded into the software of the PD cycler 100. The initial position and the distance travelled per step can then be used to determine current position at a given time during operation of the cart 50 by counting the number of motor steps. In some implementations, other calibration techniques are possible.

The table platform 58 is a substantially rigid planar member mounted to the base 52 using leg members 74. Like the vertically moveable platform 56, the table platform 58 can be formed (e.g., molded, machined, and/or cast) of any of various suitable materials (e.g., plastics, metals, and/or composites). The table platform 58 is mounted to the base 52 using the leg members 74 so that the table platform 58 is at a height that corresponds with a typical height of a patient during typical PD treatments. For example, the table platform can be positioned about 25 inches to about 30 inches (e.g., about 27 inches) above the ground surface. The leg members 74 are elongated beams that can be formed of any of various suitable materials (e.g., beams, tubing, and/or other members). The leg members 74 have sufficient column strength to support the weight of the table platform 58 along with any equipment that is typically disposed on the table platform 58. For example, the leg members can be designed to support typically about 30 lbs to about 50 lbs. As shown in FIG. 2, the table platform 58 is generally u-shaped and includes an opening 76 that is sized so that the vertically moveable platform 56 and the extension 62 are not obstructed while they move up and down along the leadscrew 64. Because the table platform 58 is u-shaped, fluid lines that extend from the front of the PD cycler 100 will typically not get hung up during use.

Referring back to FIG. 1, dialysis solution bags 122 are suspended from fingers (e.g., hooks) 123 on the sides of the cart 50, and a heater bag 124 is positioned on the heater tray 116. The dialysis solution bags 122 and the heater bag 124 are connected to the cassette 112 via dialysis solution bag lines 126 and a heater bag line 128, respectively. The dialysis solution bag lines 126 can be used to pass dialysis solution from dialysis solution bags 122 to the cassette 112 during use, and the heater bag line 128 can be used to pass dialysis solution back and forth between the cassette 112 and the heater bag 124 during use. In addition, a patient line 130 and a drain line 132 are connected to the cassette 112. The patient line 130 can be connected to a patient's abdomen via a catheter and can be used to pass dialysis solution back and forth between the cassette 112 and the patient during use. The drain line 132 can be connected to a drain or drain receptacle and can be used to pass dialysis solution from the cassette 112 to the drain or drain receptacle during use.

Peritoneal Dialysis Machine

Figure 3:
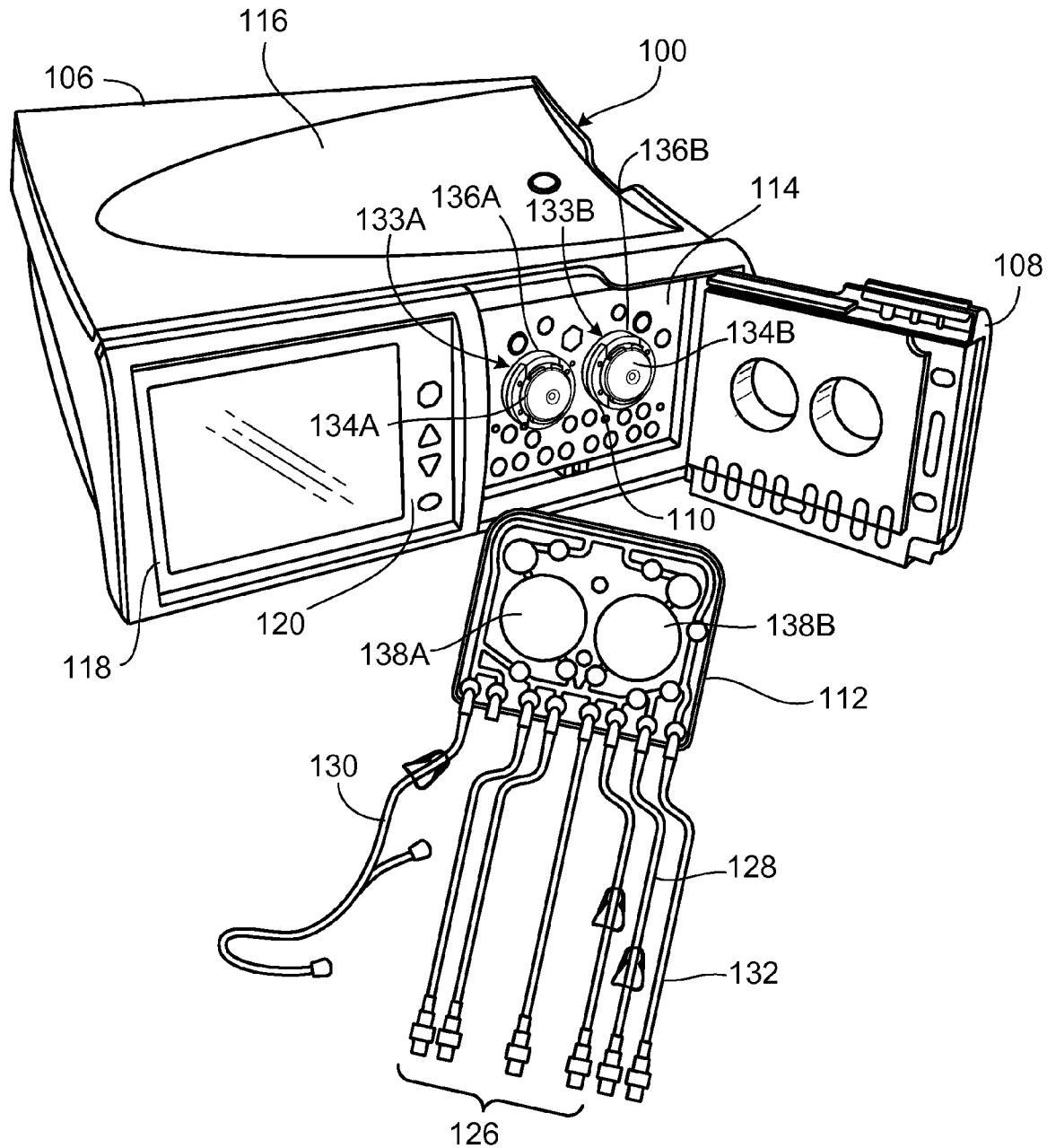
FIG. 3 is a perspective view of the PD cycler of FIG. 1 along with a PD cassette to be used with the PD cycler. A door of the PD cycler is in the open position to show the inner surfaces of the PD cycler that interface with the PD cassette during use.

As shown in FIG. 3, the PD cycler 100 includes a housing 106, a door 108, and a cassette interface 110 that abuts a disposable PD cassette 112 when the cassette 112 is disposed within a cassette compartment 114 formed between the cassette interface 110 and the closed door 108. A heater tray 116 is positioned on top of the housing 106. The heater tray 116 is sized and shaped to accommodate a bag of dialysis solution (e.g., a 5 liter bag of dialysis solution). The PD cycler 100 also includes a display (e.g., a touch screen or conventional screen) 118 and additional control buttons 120 that can be operated by a user (e.g., a patient) to allow, for example, set-up, initiation, and/or termination of a PD treatment.

Figure 4:
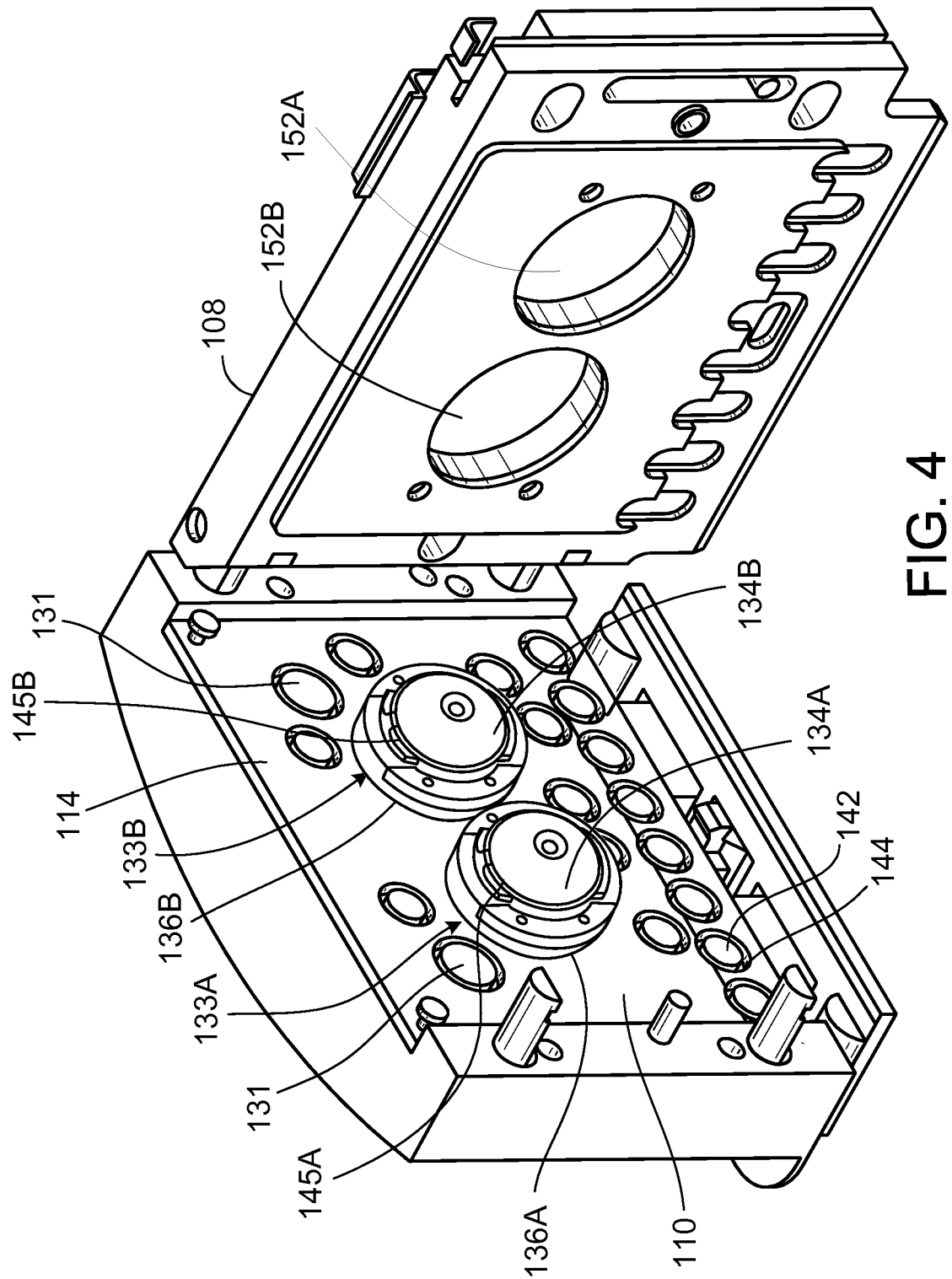
FIG. 4 is a perspective view of an open cassette compartment of the PD cycler of FIG. 1, showing, among other things, pistons having piston heads that include mechanisms that can be used to mechanically connect the piston heads to associated dome-shaped members of the PD cassette.

FIG. 4 shows a more detailed view of the cassette interface 110 and the door 108 of the PD cycler 100. As shown, the PD cycler 100 includes pistons 133A, 133B with piston heads 134A, 134B attached to piston shafts that can be axially moved within piston access ports 136A, 136B formed in the cassette interface 110. The piston shafts are connected to motors that can be operated to move the piston heads 134A, 134B axially inward and outward within the piston access ports 136A, 136B. As discussed below, when the cassette 112 (shown in FIGS. 3 and 5-7) is positioned within the cassette compartment 114 of the PD cycler 100 with the door 108 closed, the piston heads 134A, 134B of the PD cycler 100 align with pump chambers 138A, 138B of the cassette 112 such that the piston heads 134A, 134B can be mechanically connected to fastening members of the cassette 112 overlying the pump chambers 138A, 138B. As a result of this arrangement, movement of the piston heads 134A, 134B toward the cassette 112 during treatment can decrease the volume of the pump chambers 138A, 138B, and force dialysis solution out of the pump chambers 138A, 138B, while retraction of the piston heads 134A, 134B away from the cassette 112 can increase the volume of the pump chambers 138A, 138B and cause dialysis solution to be drawn into the pump chambers 138A, 138B.

Still referring to FIG. 4, the PD cycler 100 also includes multiple inflatable members 142 positioned within inflatable member ports 144 in the cassette interface 110. The inflatable members 142 align with depressible dome regions 146 of the cassette 112 (shown in FIGS. 5-7) when the cassette 112 is positioned within the cassette compartment 114 of the PD cycler 100. While only one of the inflatable members 142 is labeled in FIG. 4, it should be understood that the PD cycler 100 includes an inflatable member associated with each of the depressible dome regions 146 of the cassette 112. The inflatable members 142 act as valves to direct dialysis solution through the cassette 112 in a desired manner during use. In particular, the inflatable members 142 bulge outward beyond the surface of the cassette interface 110 and into contact with the depressible dome regions 146 of the cassette 112 when inflated, and retract into the inflatable member ports 144 and out of contact with the cassette 112 when deflated. By inflating certain inflatable members 142 to depress their associated dome regions 146 on the cassette 112, certain fluid flow paths within the cassette 112 can be occluded. Thus, PD solution can be pumped through the cassette 112 by actuating the piston heads 134A, 134B, and can be guided along desired flow paths within the cassette 112 by selectively inflating and deflating the inflatable members 142.

The door 108 of the PD cycler 100, as shown in FIG. 4, defines cylindrical recesses 152A, 152B that substantially align with the pistons 133A, 133B when the door 108 is in the closed position. When the cassette 112 (shown in FIGS. 5-7) is positioned within the cassette compartment 114, hollow projections 154A, 154B of the cassette 112, inner surfaces of which partially define the pump chambers 138A, 138B, fit within the recesses 152A, 152B. The door 108 further includes a pad that is inflated during use to compress the cassette 112 between the door 108 and the cassette interface 110. With the pad inflated, the portions of the door 108 forming the recesses 152A, 152B support the projections 154A, 154B of the cassette 112 and the planar surface of the door 108 supports the other regions of the cassette 112. The door 108 can counteract the forces applied by the inflatable members 142 and thus allows the inflatable members 142 to actuate the depressible dome regions 146 on the cassette 112. The engagement between the door 108 and the hollow projections 154A, 154B of the cassette 112 can also help to hold the cassette 112 in a desired fixed position within the cassette compartment 114 to further ensure that the pistons 133A, 133B align with the fluid pump chambers 138A, 138B of the cassette 112.

Figure 5:
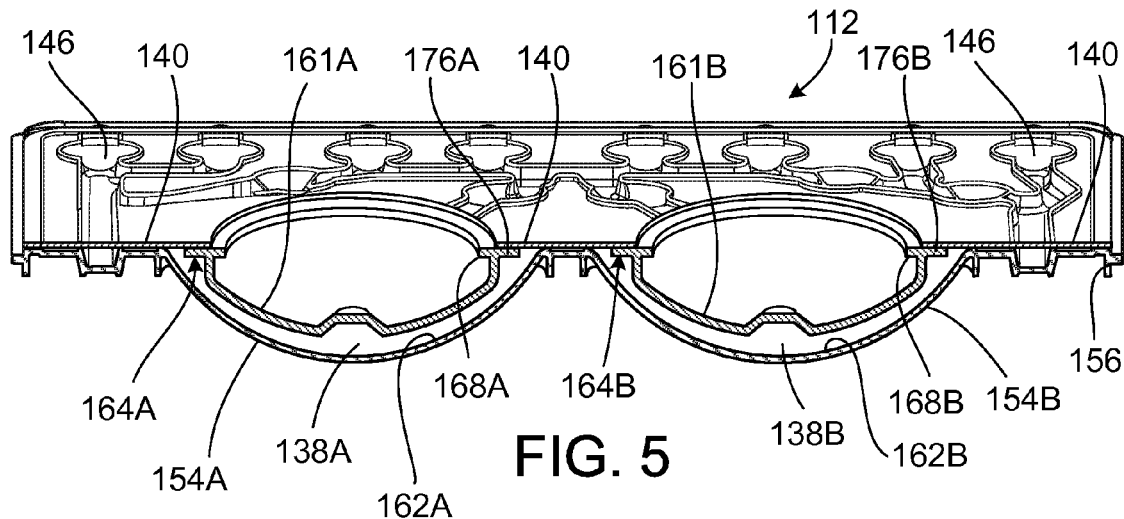
FIG. 5 is a perspective, cross-sectional view of the PD cassette of FIG. 3.
Figure 6:
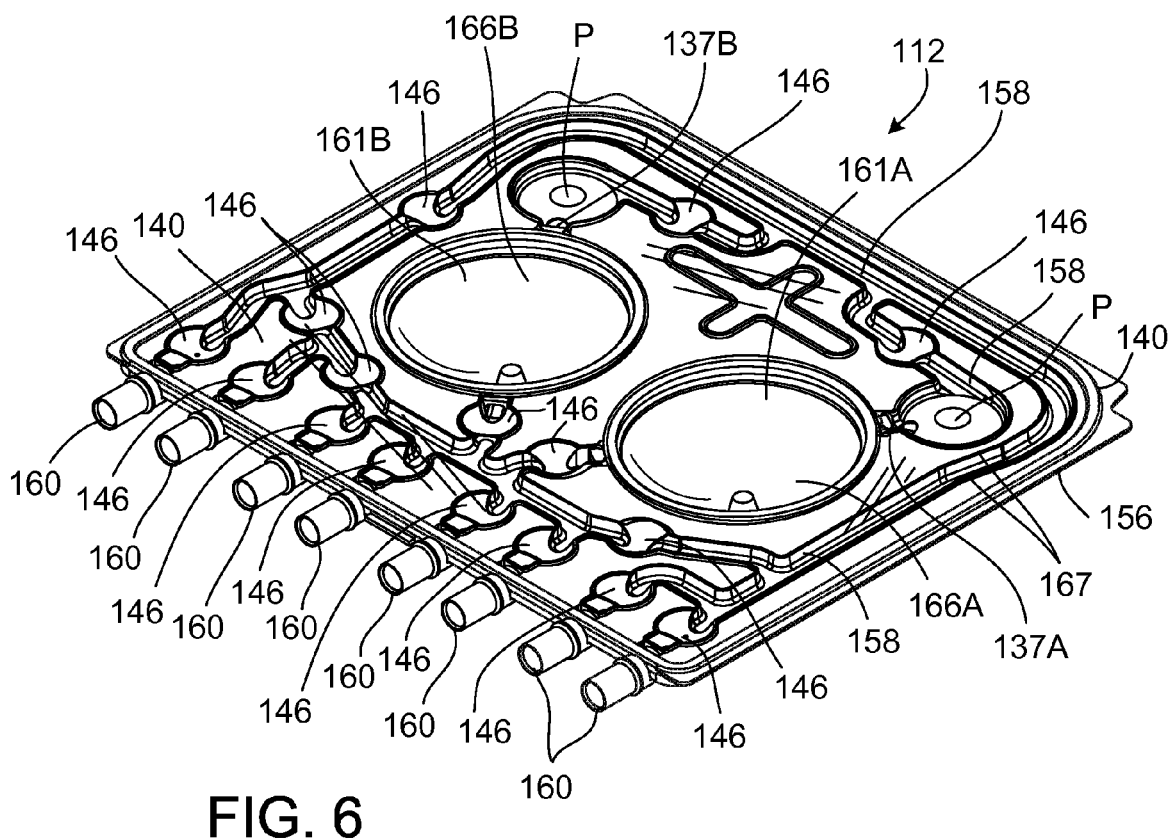
FIG. 6 is a perspective view of the PD cassette of FIG. 3, from a flexible membrane and dome-shaped fastening member side of the PD cassette.
Figure 7:
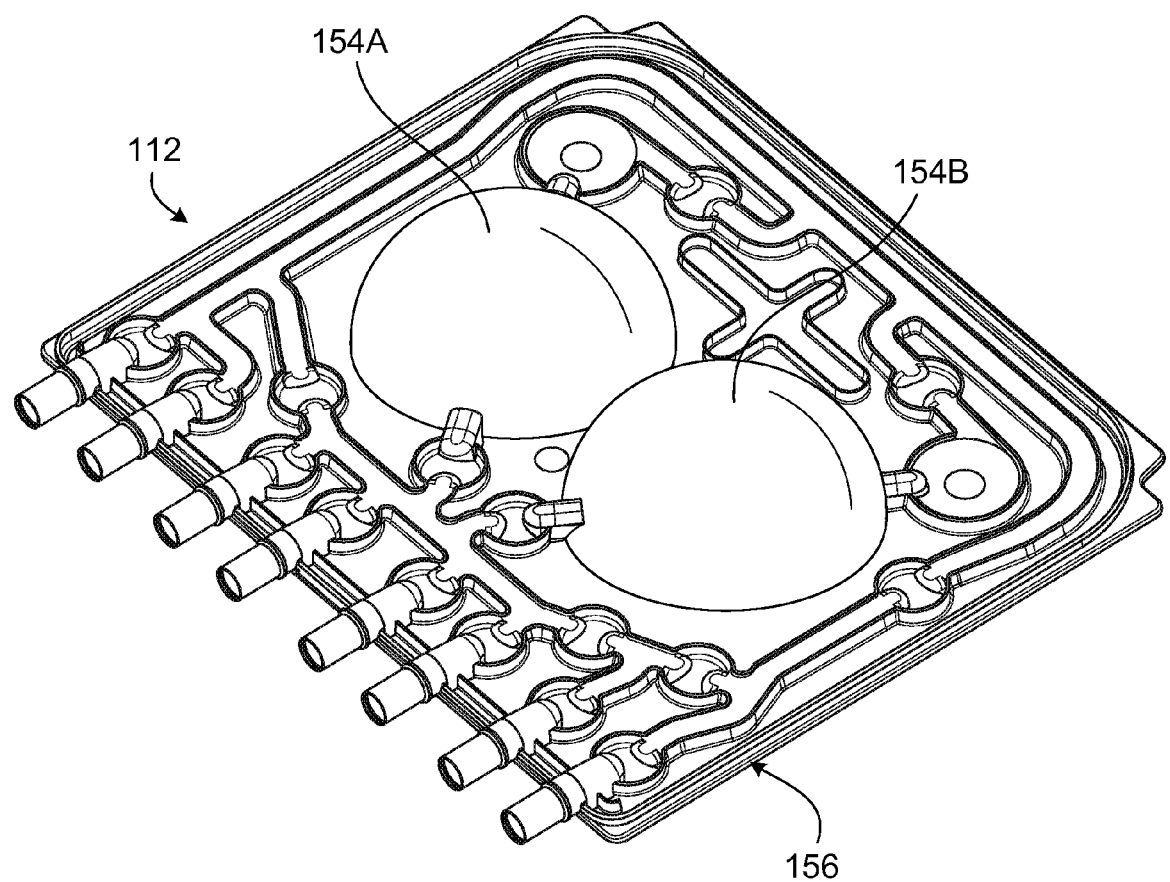
FIG. 7 is a perspective view of the PD cassette of FIG. 3, from a rigid base side of the PD cassette.

FIG. 5 is a perspective, cross-sectional view of the cassette 112, and FIGS. 6 and 7 are perspective views of the cassette 112, from the membrane side and from the rigid base side, respectively. Referring to FIGS. 5 and 6, the cassette 112 includes a flexible membrane 140 attached to a periphery of a tray-like rigid cassette base 156. Rigid dome-shaped fastening members 161A, 161B are positioned within recessed regions 162A, 162B of the cassette base 156. The dome-shaped members 161A, 161B are sized and shaped to receive the piston heads 134A, 134B of the PD cycler 100. The annular flanges 164A, 164B of the rigid dome-shaped members 161A, 161B are attached in a liquid-tight manner to portions of the inner surface of the membrane 140 surrounding substantially circular apertures 166A, 166B formed in the membrane 140. The apertures 166A, 166B expose the rigid dome-shaped members 161A, 161B such that the piston heads 134A, 134B are able to directly contact and mechanically connect to the dome-shaped members 161A, 161B during use.

The annular flanges 164A, 164B of the dome-shaped members 161A, 161B, as shown in FIG. 5, form annular projections 168A, 168B that extend radially inward and annular projections 176A, 176B that extend radially outward from the side walls of the dome-shaped members 161A, 161B. When the piston heads 134A, 134B are mechanically connected to the dome-shaped members 161A, 161B, the radially inward projections 168A, 168B engage the rear angled surfaces of the sliding latches 145A, 145B of the piston heads 134A, 134B to firmly secure the dome-shaped members 161A, 161B to the piston heads 134A, 134B. Because the membrane 140 is attached to the dome-shaped members 161A, 161B, movement of the dome-shaped members 161A, 161B into and out of the recessed regions 162A, 162B of the cassette base 156 (e.g., due to reciprocating motion of the pistons 133A, 133B) causes the flexible membrane 140 to similarly be moved into and out of the recessed regions 162A, 162B of the cassette base 156. This movement allows fluid to be forced out of and drawn into the fluid pump chambers 138A, 138B, which are formed between the recessed regions 162A, 162B of the cassette base 156 and the portions of the dome-shaped members 161A, 161B and membrane 140 that overlie those recessed regions 162A, 162B.

Referring to FIG. 6, raised ridges 167 extend from the substantially planar surface of the cassette base 156 towards and into contact with the inner surface of the flexible membrane 140 when the cassette 112 is compressed between the door 108 and the cassette interface 110 of the PD cycler 100 to form a series of fluid passageways 158 and to form the multiple, depressible dome regions 146, which are widened portions (e.g., substantially circular widened portions) of the fluid pathways 158, as shown in FIG. 6. The fluid passageways 158 fluidly connect the fluid line connectors 160 of the cassette 112, which act as inlet/outlet ports of the cassette 112, to the fluid pump chambers 138A, 138B. As noted above, the various inflatable valve members 142 of the PD cycler 100 act on the cassette 112 during use. During use, the dialysis solution flows to and from the pump chambers 138A, 138B through the fluid pathways 158 and dome regions 146. At each depressible dome region 146, the membrane 140 can be deflected to contact the planar surface of the cassette base 156 from which the raised ridges 167 extend. Such contact can substantially impede (e.g., prevent) the flow of dialysis solution along the region of the pathway 158 associated with that dome region 146. Thus, the flow of dialysis solution through the cassette 112 can be controlled through the selective depression of the depressible dome regions 146 by selectively inflating the inflatable members 142 of the PD cycler 100.

Still referring to FIG. 6, fluid line connectors 160 are positioned along the bottom edge of the cassette 112. As noted above, the fluid pathways 158 in the cassette 112 lead from the pumping chambers 138A, 138B to the various connectors 160. The connectors 160 are configured to receive fittings on the ends of the dialysis solution bag lines 126, the heater bag line 128, the patient line 130, and the drain line 132. One end of the fitting can be inserted into and bonded to its respective line and the other end can be inserted into and bonded to its associated connector 160. By permitting the dialysis solution bag lines 126, the heater bag line 128, the patient line 130, and the drain line 132 to be connected to the cassette, as shown in FIGS. 1 and 3, the connectors 160 allow dialysis solution to flow into and out of the cassette 112 during use.

As noted above, the membrane 140 is attached to the periphery of the cassette base 156 and to the annular flanges 164A, 164B of the dome-shaped members 161A, 161B. The portions of the membrane 140 overlying the remaining portions of the cassette base 156 are typically not attached to the cassette base 156. Rather, these portions of the membrane 140 sit loosely atop the raised ridges 165A, 165B, and 167 extending from the planar surface of the cassette base 156.

The technique and pumping operation used to draw dialysis solution into the pump chamber 138A and to force dialysis solution out of the pump chamber 138A and that of pump chamber 138B are identical and thus such techniques and operations are discussed with regards to pump chamber 138A and are not separately described in detail with regards to pump chamber 138B.

Figure 8:
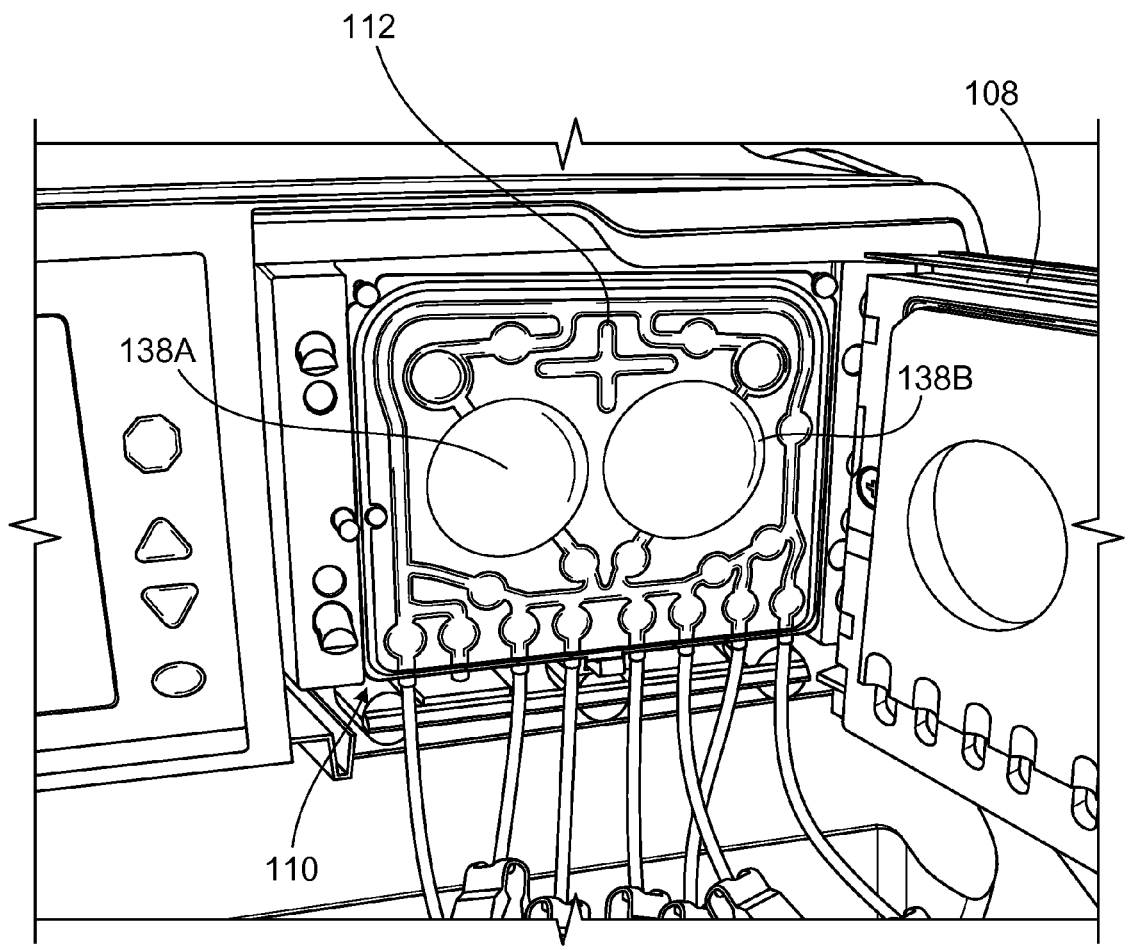
FIG. 8 is a partial perspective view of the PD cassette in the cassette compartment of the PD cycler FIG. 3.

As shown in FIG. 8, during installation, the door 108 of the PD cycler 100 is opened to expose the cassette interface 110 and the cassette 112 is positioned adjacent to the cassette interface 110 with dome-shaped members 161A, 161B aligned with the pistons 133A, 133B of the PD cycler 100 and with its membrane 140 adjacent to the cassette interface 110. The pistons 133A, 133B are typically retracted into the piston access ports 136A, 136B during installation of the cassette 112 to avoid interference between pistons 133A, 133B and the dome-shaped members 161A, 161B and thus increase the ease with which the cassette 112 can be positioned within the cassette compartment 114. Once the cassette 112 is properly in position, the door 108 can be closed over the cassette 112 such that the cassette 112 is contained within the cassette compartment 114 between the door 108 and the cassette interface 110. With the cassette 112 positioned in the cassette compartment 114 and the door 108 closed, the inflatable pad within the door 108 is inflated to compress the cassette 112 between the door 108 and the cassette interface 110. This compression of the cassette 112 holds the projection 154A of the cassette 112 in the recess 152A of the door 108 and presses the membrane 140 tightly against the raised ridges 167 extending from the planar surface of the rigid base 156 to form the enclosed fluid pathways 158 and dome regions 146.

Once the cassette 112 has been installed within the cassette compartment 114 of the PD cycler 100, the piston 133A is advanced to initiate the process of mechanically connecting the piston head 134A of the PD cycler 100 to the dome-shaped member 161A of the cassette 112. The piston 133A includes a latch-type device that engages the dome shaped member 161A. To engage the latch-type device, the piston 133A continues to advance toward the cassette 112 until latches contact and engage the dome shaped member 161A for operation of the PD cycler.

After the piston 133A has been mechanically connected to the dome-shaped member 161A, the piston 133A is retracted to draw dialysis solution into the pump chamber 138A. Because the piston head 134A is mechanically connected to the dome-shaped member 161A and the dome-shaped member 161A is attached to the membrane 140 of the cassette 112, the retraction of the piston 133A causes the dome-shaped member 161A and the portion of the membrane 140 attached to the dome-shaped member 161A to move rearwardly. As a result, the volume of the pump chamber 138A is increased and fluid is drawn into the pump chamber 138A.

Because the volumes of the fluid pump chamber 138A and the piston head 134A are known, the linear distance travelled by the piston 133A can be used to determine the volume of dialysis solution drawn into the fluid pump chamber 138A. The linear distance travelled by the piston 133A can be determined based on the number of revolutions or steps of the motor (e.g., stepper motor) used to drive the piston 133A. Thus, the volume of solution drawn into the fluid pump chamber 138A can be determined based on the number of revolutions or steps of the motor. The tight fit between the piston head 134A and the dome-shaped member 161A ensure the accuracy of the volume of solution determined in this manner.

After drawing the dialysis solution into the pump chamber 138A, the dialysis solution is forced out of the pump chamber 138A by again advancing the piston 133A and decreasing the volume of the pump chamber 138A. The piston 133A is typically advanced until the dome-shaped member 161A contacts or nearly contacts the inner surface of the recessed region of the cassette base 156 so that substantially all of the dialysis solution is forced out of the fluid pump chamber 138A via the outlet port 187A.

This process of drawing dialysis solution into the fluid pump chamber 138A and then forcing the dialysis solution out of the fluid pump chamber 138A is repeated until a desired volume of dialysis solution has been pumped to or from a location (e.g., to or from the patient).

As noted above, while forcing dialysis solution into and out of the pump chambers 138A, 138B, certain inflatable members 142 of the PD cycler 100 can be selectively inflated to direct the pumped dialysis solution along desired pathways in the cassette 112.

Referring back to FIGS. 1 and 3, during PD treatment, the patient line 130 is connected to a patient's abdomen via a catheter, and the drain line 132 is connected to a drain or drain receptacle. The PD treatment typically begins by emptying the patient of spent dialysis solution that remains in the patient's abdomen from the previous treatment. To do this, the pump of the PD cycler 100 is activated to cause the pistons 133A, 133B to reciprocate and selected inflatable members 142 are inflated to cause the spent dialysis solution to be drawn into the fluid pump chambers 138A, 138B of the cassette 112 from the patient. The spent dialysis solution is then pumped from the fluid pump chambers 138A, 138B to the drain via the drain line 132.

After draining the spent dialysis solution from the patient, heated dialysis solution is transferred from the heater bag 124 to the patient. To do this, the motor or motors of the PD cycler 100 is/are activated to cause the pistons 133A, 133B to reciprocate and certain inflatable members 142 of the PD cycler 100 are inflated to cause the warmed dialysis solution to be drawn into the fluid pump chambers 138A, 138B of the cassette 112 from the heater bag 124 via the heater bag line 128. The warmed dialysis solution is then pumped from the fluid pump chambers 138A, 138B to the patient via the patient line 130.

Once the dialysis solution has been pumped from the heater bag 124 to the patient, the dialysis solution is allowed to dwell within the patient for a period of time. During this dwell period, toxins cross the peritoneum of the patient into the dialysis solution from the patient's blood. As the dialysis solution dwells within the patient, the PD cycler 100 prepares fresh dialysate for delivery to the patient in a subsequent cycle. In particular, the PD cycler 100 pumps fresh dialysis solution from one of the four full dialysis solution bags 122 into the heater bag 124 for heating. To do this, the pump of the PD cycler 100 is activated to cause the pistons 133A, 133B to reciprocate and certain inflatable members 142 of the PD cycler 100 are inflated to cause the dialysis solution to be drawn into the fluid pump chambers 138A, 138B of the cassette 112 from the selected dialysis solution bag 122 via its associated line 126. The dialysis solution is then pumped from the fluid pump chambers 138A, 138B to the heater bag 124 via the heater bag line 128.

After the dialysis solution has dwelled within the patient for the desired period of time, the spent dialysis solution is pumped from the patient to the drain. The heated dialysis solution is then pumped from the heater bag 124 to the patient where it dwells for a desired period of time. These steps are repeated with the dialysis solution from two of the three remaining dialysis solution bags 122. The dialysis solution from the last dialysis solution bag 122 is typically delivered to the patient and left in the patient until the subsequent PD treatment.

After completion of the PD treatment, the pistons 133A, 133B are retracted in a manner to disconnect the piston heads 134A, 134B from the dome-shaped members 161A, 161B of the cassette.

After the pistons 133A, 133B have been disconnected from and backed out of the dome-shaped members 161A, 161B of the cassette 112 in the manner described above, the door 108 of the PD cycler is opened and the cassette 112 is removed from the cassette compartment 114 and discarded.

Monitoring Fluid Pressure

It is advantageous to be able to accurately monitor and control pressure between the pump chambers 138A, 138B of the cassette 112 and the patient. If the pressure within a line to the patient increases above maximum limits, harm can be caused to the patient.

To monitor the pressure in the system, two pressure sensors 131 (shown in FIG. 4) are utilized to indirectly detect the pressure and vacuum within the patient's peritoneum. These sensors are preferably solid state silicon diaphragm infusion pump force/pressure transducers, for example Model 1865 made by Sensym Foxboro ICT. When the cassette 112 (shown in FIGS. 3 and 5-8) is inserted into the cassette compartment 114, the pressure sensing areas "P" within the cassette 112 (shown in FIG. 6) line up and are in intimate contact with the two pressure sensors 131. These sensing areas P are connected, respectively, directly to each pump chamber 138A, 138B through canals 137A and 137B, respectively, so that when fluid moves in and out of the chambers 138A, 138B, the pressure sensors 131 can detect its presence. The cassette membrane includes two areas marked "P" adheres to the pressure sensors 131 using vacuum pressure. Clearance around the pressure sensors communicates vacuum to the pressure dome diaphragms the circumferences of which are sealed airtight to the cassette deck by the pressurization of the door compartment.

The two pressure sensors 131 are connected to a high resolution 24 bit Sigma-Delta, serial output A-D converter (ADC) on an I/O board. This ADC sends a signal from each of the two pressure sensors to the FPGA on the board. After the data ready signal is received by the FPGA, the FPGA reads this ADC and transfers this data to be processed by the microprocessor, which in the preferred implementation of the invention is an MPC823 PowerPC device manufactured by Motorola, Inc.

On completion of the flush and prime processes, the cassette will be filled with solution. At this time, the line to the patient will be completely filled with solution. The pressure at this stage is detected and will be used as base line for static pressure. At that time, the patient's head height relative to the PD cycler will be determined from the differential in the pressure reading. Preferably, this pressure differential is maintained below 100 mbar.

During the drain sequence, it is advantageous to hold the vacuum in the peritoneum at or above −100 mbar.

Since continuous flow through the various lines connected to the patient is essential to proper treatment of the patient, it is important to continuously monitor if a patient line is blocked, partially blocked or open. There are three different possible situations:
 1. the patient line is open;
 2. the patient line is closed; or
 3. the patient line is not completely open and therefore creates an undesired flow resistance (caused, for example by the patient is lying on the line).

The pressure sensors 131 (shown in FIG. 4) can be used to detect error conditions. For example, when the piston 133A is protracting and thereby pumping dialysate fluid into a line that is open to patient, it is advantageous that the patient pressure and the encoder values can be carefully monitored, using the pressure sensors 131 described above. Three possible error situations may occur, for example, as a result of the following events:
 1. The patient line is open when piston 133A is protracting until a defined length value is reached, and the patient pressure is not increasing;
 2. The patient line is closed, and the piston 133A is not able to protract because the patient pressure increases to a defined alarm limit.
 3. The piston 133A protracts to produce an increasing patient pressure, but the pressure decreases slowly.

These error conditions may be sensed using the pressure sensors 131, and corrective action can then be taken. Although corrective action could be in the form of sending an alarm to the patient, where the screen tells the patient what action to take, utilizing the methods described herein can address some errors automatically without disturbing the patient.

Cart Uses

During PD treatments fluid resistance can build within the line that is connected to a patient's abdomen via a catheter and used to pass dialysis solution back and forth between the cassette and the patient. Such resistance can be caused by several factors, such as kinks in the patient line caused by the patient lying on the line or other external line obstructions, excess levels of fibrin present in the patient line, catheter obstructions within the patient's abdomen, and/or other issues. As discussed above, the resistance within the patient line can be detected using the pressure sensors that measure the pressure in pump chambers 138A, 138B. Typically, when the pressure builds in the patient line to a level that may be dangerous to the patient (e.g., 150-200 mbar), an alarm will sound indicating that an error exists and needs to be addressed. In some cases, an audible alarm will sound that will awaken the patient undergoing PD treatment so that the patient can address the problem (e.g., by adjusting the line or taking alternate action). This awakening of the patient can result in an uncomfortable, disturbing, and/or undesirable PD treatment. Alternatively to sounding an alarm, the PD cycler pumps can be turned off to allow the pressure to reduce to acceptable levels. However, turning off the PD cycler pumps also results in delayed or incomplete and therefore sometimes equally undesirable PD treatment. Therefore, any reduction in the frequency of such alarms or interruptions to the PD treatment by automatically addressing the errors can provide a more comfortable and, in some cases, a safer PD treatment for the patient.

The cart 50 described herein can be used to automatically address some errors that occur during PD treatments caused by resistance in the patient line. In order to automatically address errors, as shown in FIG. 1, the PD cycler 100 is seated on the vertically moveable platform 56 that is positioned at a home position (e.g., along the plane of the table platform 58) at substantially the same height as the patient. As discussed below, the PD cycler 100 can be raised and/or lowered using the drive assembly 60 to accommodate for pressure build-up during filling and/or draining of PD solution during treatments.

When high resistance levels are detected by the pressure sensors 131 during filling, the PD cycler 100 can automatically reduce the pump speeds to prevent the pressure from continuing to increase to levels that could be potentially dangerous. However, in doing so, reducing the pump speeds can also cause the PD solution flow rates to decrease, and in some cases the flow to the patient can cease. Therefore, to maintain flow of PD solution to the patient while the pump speed is lowered, the vertically moveable platform 56 is raised to a height that is above the patient so that the static pressure difference within the patient line will cause the flow rate to increase or to be maintained at desired levels.

Similarly, when high resistance levels are detected by the pressure sensors 131 during draining, the PD cycler 100 can automatically reduce the pump speeds to prevent the pressure from continuing to increase to levels that could potentially be dangerous. Like during filling, reducing the pump speeds can cause the flow rate of PD solution from the patient to begin to decrease. However, instead of raising the PD cycler 100 using the drive assembly 60 as done during filling, the cart 50 lowers the PD cycler 100 to a height that is below the patient. By lowering the PD cycler 100, the static pressure difference within the patient line will cause the flow rate of PD solution from the patient to increase or to be maintained at desired levels.

Example of Use of PD Cycler on a Cart During Draining

In one example of a PD treatment, during a normal draining process, PD solution flows from a patient at an average flow rate of 200 ml/minute and at an average pressure of 60-70 mbar, during which the pump of the PD cycler 100 is operated at a pump speed of 80. The pump speed is associated with the rate of at which a leadscrew within the pump is rotated to move the pistons 133A, 133B in and out of the pump chamber, which can range from 5-140 during operation, for example, when using a Liberty PD cycler from Fresenius Medical Care NA.

During PD treatments, as discussed herein, certain events can occur (e.g., a line can become kinked or a catheter can become positioned against an obstruction in the patient) that cause resistance that opposes the fluid from draining from a patient and causes pressure to build within the patient line. As fluid resistance continues to build within the patient line, the pressure that is measured within the pump chamber will also continue to increase. Instead of waking up the patient or sounding an alarm to address the issue before the pressure level reaches a dangerous level (e.g., 150-200 mbar), as would typically be done when using certain conventional PD systems, the PD cycler pumps are slowed gradually (e.g., by increments of 10) to reduce the high dynamic pressure caused by the fluid flow in the patient line. The pump speed can be reduced by 10 while the pressure within the line is continuously monitored. If the pressure does not drop to within acceptable limits (e.g., less than 150 mbar), the pump speed is again reduced by 10 and the pressure within the line is monitored. While monitoring the pressure, the pump speed is reduced incrementally until the pressure drops to within acceptable limits (e.g., less than 150 mbar). However, when the PD cycler 100 is held at a constant vertical height, reducing the pump speed typically causes the flow rate to decrease. For example, a pump speed reduction of 5-10 can result in a flow rate drop of about 20 ml/min and a pump speed reduction of 40 to 50 can result in a flow rate drop of about 100 ml/min. Since reducing the pumps speed typically reduces the flow rate, the PD cycler 100 seated on the vertically moveable platform 56 is lowered below the patient (e.g., 5 inches-20 inches) gradually to increase or maintain the flow rate (e.g., within 150 ml/min to 200 ml/min) of fluid draining from the patient. Lowering the PD cycler 100 allows for draining fluid from the patient at a higher fluid flow rate, while avoiding dangerously high pressures and/or disruption to the patient. Since the PD cycler 100 is able to control and monitor the position of the vertically moveable platform 56 and the operation of the pump, the PD cycler 100 controls the position of vertically moveable platform 56 and the pump speed to improve (e.g., optimize) the PD treatment by increasing (e.g., maximizing) the flow rate while keeping the pressure below excessive levels.

During the PD treatment, if the obstruction is removed and the resistance in the patient line is therefore reduced, the PD cycler 100 can either allow the vertically moveable platform 56 to remain at the lowered height or raise the vertically moveable platform 56 to bring the PD cycler 100 back to a home position that is approximately level with the patient. Instead of turning down the pumps and then adjusting the height of the PD cycler 100 to compensate for the loss of fluid flow, alternatively, the PD cycler 100 can begin moving the vertically moveable platform 56 and the PD cycler 100 downward while simultaneously slowing the pumps so that the loss of flow is minimized, in some cases there is no loss of fluid flow.

While certain implementations have been described, other implementations are possible.

While the drive assembly has been described as including a stationary leadscrew and a rotating leadscrew nut, other configurations can be used. For example, in some implementations, the cart includes a leadscrew that can rotate and a leadscrew nut that is fixed to the vertically moveable platform.

While the drive assembly has been described as including a leadscrew assembly to move the vertically moveable platform, other devices can be used. In some implementations, the drive assembly includes a rack and pinion gear system, where the rack is positioned vertically and the pinion gear is mounted in the vertically moveable platform.

While the alignment mechanism has been described as including a recess in the leadscrew and a tab extending from a portion of the vertically moveable platform, other alignment techniques can be used. In some cases, the drive assembly does not require an alignment mechanism.

In some implementations, the vertically moveable platform includes a retention device (e.g., a strap, screws, bolts, etc.) to secure the PD cycler during articulation.

While the PD cycler has been described as monitoring the position of the vertically moveable platform by counting the number of rotations of the motor which drives the drive assembly, other techniques can be used. For example, in some implementations, the drive assembly or vertically moveable platform includes position sensors to determine the vertical position of the vertically moveable platform.

While the motor has been described as being electrically connected to the PD cycler in order to control the motor, other techniques can be used. In some implementations, referring to FIG. 2, the motor 68 is electrically connected to a separate control unit 63 that is used to operate the motor 68 and control the position of the vertically moveable platform 56.

While the motor has been described as being connected to the leadscrew nut using gears, other techniques can be used. In some implementations, the drive assembly is driven by the motor using pulleys, chains, or other suitable techniques. Alternatively, in some implementations, the motor is an integrated component of the drive assembly.

While the cart has been described as including a table platform, in some implementations, the cart does not include a table platform.

While the cart has been described as including three wheels, the cart can include more or fewer wheels. For example, carts can include 2, 4, 5, 6, or more wheels.

While the wheels have been described as being casters, other types of suitable wheels can be used.

In some implementations, one or more of the wheels include a locking mechanism to temporarily secure the cart in place.

Alternatively, in some implementations, the cart does not include wheels.

While the piston heads have been described as including mechanical latch mechanisms with sliding latches that can be move radially inward and outward to allow those piston heads to be mechanically connected to dome-shaped members of the cassette, other piston heads can alternatively be used. In some implementations, other piston heads utilizing other mechanical engagement mechanisms of simpler construction that include no such sliding latches can alternatively be used in some cases. Alternatively, piston heads utilizing other engagement techniques (e.g., vacuum systems, adhesives, magnetics, or any other suitable techniques) can be used to couple the pistons to the dome-shaped members of the cassette or to the membrane of the cassette.

While the cassettes discussed above have two pump chambers, the cassettes can alternatively have more or fewer than two pump chambers.

While each of the pump chambers of the cassettes described above has been described as including a fluid inlet port and a fluid outlet port, in certain implementations, the pump chambers include a single port that is used as both an inlet and an outlet. In such implementations, the inflatable valve members of the PD cycler that act on the valve portions of the cassettes would be activated and deactivated in a slightly different sequence to allow fluid to be drawn into the pump chamber from a desired location and then to be forced out of the pump chamber to a desired location.

While the carts described above has been described as being associated with PD systems, these types of carts can be used in any of various other types of medical fluid pumping systems. Other examples of medical fluid pumping systems in which the carts described herein can be used include hemodialysis systems, blood perfusion systems, intravenous infusion systems, and other medical fluid handling systems.

What is claimed is:

1. A dialysis machine support assembly comprising:
    a platform configured to support a dialysis machine;
    a drive assembly configured to move the platform vertically; and
    a control unit configured to
        monitor input data from a sensor that is disposed along a fluid path between a dialysis fluid pump chamber of the dialysis machine and a patient during treatment, when the dialysis machine is supported by the platform, and
        operate the drive assembly to adjust a vertical position of the platform based on the input data.

2. The dialysis machine support assembly of claim 1, wherein the drive assembly can move the platform along a vertical distance that is 24-48 inches.

3. The dialysis machine support assembly of claim 1, further comprising a device configured to prevent the platform from rotating about the drive assembly when the platform moves vertically.

4. The dialysis machine support assembly of claim 1, wherein the drive assembly comprises:
    a leadscrew fixed to a base;
    a leadscrew nut that is rotatably coupled to the platform and configured to engage the leadscrew; and
    a motor that is mechanically connected to the leadscrew nut and configured to rotate the leadscrew nut.

5. The dialysis machine support assembly of claim 4, wherein the motor is an electric motor configured to be electrically connected to the control unit.

6. The dialysis machine support assembly of claim 4, wherein:
    the leadscrew has a recess formed longitudinally along the leadscrew; and
    the platform has a tab that is sized to fit within the recess and travel along the recess when the platform moves vertically.

7. The dialysis machine support assembly of claim 1, further comprising:
    multiple legs; and
    a stationary platform disposed on top of the multiple legs.

8. The dialysis machine support assembly of claim 7, further comprising a base from which the multiple legs extend upwardly.

9. The dialysis machine support assembly of claim 8, further comprising multiple wheels secured to a bottom of the base to support the dialysis machine support assembly.

10. The dialysis machine support assembly of claim 1, wherein the sensor is a pressure sensor, and the input data is pressure data.

11. The dialysis machine support assembly of claim 10, wherein the control unit adjusts the vertical position of the platform when the pressure data exceeds a maximum pressure or falls below a minimum pressure.

12. The dialysis machine support assembly of claim 11, further comprising;
    a base from which the drive assembly upwardly extends; and
    a stationary platform located above the base and fixed relative to the base,
    wherein the drive assembly is configured to adjust the vertical position of the platform to a first height that is above the stationary platform and to a second height that is below the stationary platform, and the platform is configured to move through a recess defined by the stationary platform.

13. A dialysis system comprising:
    a dialysis machine; and
    a dialysis machine support assembly comprising:
        a platform configured to support the dialysis machine; and
        a drive assembly configured to move the platform vertically,
    wherein the dialysis machine is disposed on the platform,
    wherein the dialysis machine or the dialysis machine support assembly comprises a control unit configured to
        monitor input data from a sensor of the dialysis machine, and
        operate the drive assembly to adjust a vertical position of the platform based on the input data.

14. The dialysis system of claim 13, wherein the dialysis machine is a peritoneal dialysis cycler.

15. The dialysis system of claim 13, wherein the sensor is a pressure sensor, and the input data is pressure data.

16. The dialysis system of claim 15, wherein the control unit adjusts the vertical position of the platform when the pressure data exceeds a maximum pressure or falls below a minimum pressure.

17. The dialysis system of claim 16, further comprising:
a base from which the drive assembly upwardly extends; and
a stationary platform located above the base and fixed relative to the base,
wherein the drive assembly is configured to adjust the vertical position of the platform to a first height that is above the stationary platform and to a second height that is below the stationary platform, and the platform is configured to move through a recess defined by the stationary platform.

18. The dialysis system of claim 13, wherein the sensor is disposed along a fluid path between a dialysis fluid pump chamber of the dialysis machine and a patient.

19. The dialysis system of claim 13, wherein the control unit comprises a microprocessor of the dialysis machine.

20. A dialysis machine support assembly, comprising:
a base;
multiple wheels disposed along a bottom surface of the base;
a drive assembly extending upward from the base;
a vertically moveable platform secured to a moving portion of the drive assembly, the vertically moveable platform being configured to support a dialysis machine, and a vertical position of the vertically moveable platform being controlled by the drive assembly;
multiple legs extending upward from the base;
a stationary platform disposed on top of the multiple legs, the stationary platform defining a recess that is sized to receive the vertically moveable platform;
multiple hooks extending from sides of the stationary platform, the hooks being configured to support dialysate bags fluidly connected to the dialysis machine during a dialysis treatment; and
a control unit configured to
monitor input data from a sensor that is disposed along a fluid path between a dialysis fluid pump chamber of the dialysis machine and a patient during treatment, when the machine is supported by the vertically moveable platform, and
operate the drive assembly to adjust the vertical position of the vertically moveable platform based on the input data,
wherein, the drive assembly is configured to move the vertically moveable platform above and below a height at which the patient is positioned during the dialysis treatment.

21. The dialysis machine support assembly of claim 20, wherein the sensor is a pressure sensor, and the input data is pressure data.

22. The dialysis machine support assembly of claim 21, wherein the control unit adjusts the vertical position of the vertically moveable platform when the pressure data exceeds a maximum pressure or falls below a minimum pressure.

23. The dialysis machine support assembly of claim 22, wherein the stationary platform is located above the base and fixed relative to the base, the drive assembly is configured to adjust the vertical position of the vertically moveable platform to a first height that is above the stationary platform and to a second height that is below the stationary platform, and the vertically movable platform is configured to move through the recess defined by the stationary platform.

* * * * *